(12) United States Patent
Kim et al.

(10) Patent No.: US 9,879,122 B2
(45) Date of Patent: Jan. 30, 2018

(54) SUPER ABSORBENT POLYMER AND METHOD OF PREPARING THE SAME

(71) Applicants: SK INNOVATION CO., LTD, Seoul (KR); SK GLOBAL CHEMICAL CO., LTD., Seoul (KR)

(72) Inventors: Ju-Hee Kim, Daejeon (KR); Du-Youn Ka, Daejeon (KR); Byoung-Tak Yim, Daejeon (KR); Byoung-Cheon Jo, Seoul (KR)

(73) Assignees: SK INNOVATION CO., LTD., Seoul (KR); SK GLOBAL CHEMICAL CO., LTD., Seoul (KR)

( * ) Notice: Subject to any disclaimer, the term of this patent is extended or adjusted under 35 U.S.C. 154(b) by 229 days.

(21) Appl. No.: 15/011,713

(22) Filed: Feb. 1, 2016

(65) Prior Publication Data

US 2016/0222175 A1   Aug. 4, 2016

(30) Foreign Application Priority Data

Jan. 30, 2015 (KR) .................. 10-2015-0014937

(51) Int. Cl.
| | | |
|---|---|---|
| C08F 8/46 | (2006.01) | |
| C08J 3/24 | (2006.01) | |
| A61L 15/24 | (2006.01) | |
| C08F 220/06 | (2006.01) | |

(52) U.S. Cl.
CPC .............. *C08J 3/245* (2013.01); *A61L 15/24* (2013.01); *C08F 8/46* (2013.01); *C08F 220/06* (2013.01); *C08J 2333/02* (2013.01)

(58) Field of Classification Search
CPC ............. C08J 2205/022; C08J 2400/14; C08J 2300/14; C08J 3/245; C08F 265/02
See application file for complete search history.

(56) References Cited

U.S. PATENT DOCUMENTS

| 6,914,099 B2 | 7/2005 | Kim |
| 2013/0090442 A1 | 4/2013 | Pugh et al. |

FOREIGN PATENT DOCUMENTS

| JP | 2013-132434 A | 7/2013 |
| KR | 10-2013-0120400 A | 11/2013 |

OTHER PUBLICATIONS

Office action dated May 22, 2015 from Korean Intellectual Property Office in a counterpart Korean Patent Application No. 10-2015-0014937.
Notice of Allowance dated Jan. 11, 2016 from Korean Intellectual Property Office in a counterpart Korean Patent Application No. 10-2015-0014937.
Afsaneh Nabifar et al., "Insights Into Crosslinking Nitroxide-Mediated Radical Copolymerization of Styrene and Divinylbenzene with a Unimolecular Initiator", Alche Annual Meeting, 2011 (abstract is submitted.).
Kejian Bian et al., "Nitroxide-Mediated Radical Polymerization of 2-(Dimethylamino)ethyl Acrylate and Its Sequential Block Copolymerization with Styrene and N-Butyl Acrylate", Journal of Polymer Science, vol. 44, p. 414-426, 2006.

*Primary Examiner* — Mark S Kaucher
(74) *Attorney, Agent, or Firm* — The PL Law Group, PLLC

(57) ABSTRACT

A super-absorbent polymer satisfying Equation 1 exhibits remarkably improved shape rupture under pressure while maintaining excellent absorption ability. The super-absorbent polymer may be prepared by preparing a base resin by polymerizing a polymeric compound containing an acrylic monomer by using a polyfunctional nitroxide mediated radical polymerization initiator, substituting a terminal of the polymer prepared in the polymerization step with maleic anhydride, cross-linking each maleic anhydride terminal of different polymers prepared in the substitution step by using alkylenediamine having 2 to 8 carbon atoms, drying and grinding the base resin, and surface cross-linking the ground base resin.

4 Claims, No Drawings

SUPER ABSORBENT POLYMER AND METHOD OF PREPARING THE SAME

CROSS-REFERENCE TO RELATED APPLICATION

This application claims priority to and the benefit of Korean Patent Application No. 10-2015-0014937, filed on Jan. 30, 2015, the disclosure of which is incorporated herein by reference in its entirety.

BACKGROUND

1. Field of the Invention

The present invention relates to a super-absorbent polymer and a method of preparing the same.

2. Description of the Related Art

A super-absorbent polymer is a functional resin having an ability of absorbing water of several tens to thousands of times the weight of the polymer and keeping the same therein, and thus, is broadly used in various products including hygienic products such as a paper (disposable) diaper, sanitary goods, medical patches, agricultural absorbents, absorptive pads for foodstuffs, cable protective films, or the like.

The super-absorbent polymer is generally used in a powder form, and when it is applied to a product, it is usually used in combination with a fibrous substrate made of natural fiber such as non-woven fabric, pulp, etc. or synthetic fiber to form an absorbent material.

U.S. Pat. No. 6,914,099 discloses a method of preparing absorbent polymer particles based on cross-linked carboxyl containing polymer with a low monomer content, which includes polymerizing a polymer mixture including an ethylene unsaturated carboxyl containing monomer, a cross-linking agent, a comonomer copolymerisable with the carboxyl containing monomer, and a polymerization medium to form a cross-linked hydrogel.

However, since an internal cross-linking agent has higher reactivity than the carboxyl containing monomer, the internal cross-linking agent is exhausted at an initial stage of the reaction, or an acryl internal cross-linking agent has a low solubility in water used as a solvent to cause a difficulty in producing a uniform polymer composition, and therefore, it is hard to expect a uniform internal cross-linking structure.

SUMMARY

An aspect of the present invention is to provide a super-absorbent polymer with remarkably improved shape rupture under pressure while retaining excellent absorption ability, as well as a method of preparing the same.

The above aspect of the present invention will be achieved by the following characteristics:

(1) A method of preparing a super-absorbent polymer, including polymerization, drying, grinding and surface cross-linking processes, wherein the polymerization process includes: polymerizing a polymeric compound containing an acrylic monomer by using a polyfunctional nitroxide mediated radical polymerization initiator, which contains at least three substituents represented by Formula 1 below:

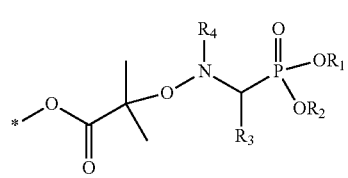

[Formula 1]

(wherein * denotes a dangling bond, and $R_1$, $R_2$, $R_3$ and $R_4$ are each independently alkyl group having 1 to 6 carbon atoms);

substituting a terminal of the polymer prepared in the polymerization step with maleic anhydride; and cross-linking each maleic anhydride terminal of different polymers prepared in the substitution step by using alkylenediamine having 2 to 8 carbon atoms.

(2) The method according to the above (1), wherein the alkylenediamine is 1,5-pentanediamine.

(3) A super-absorbent polymer having a water-retention ability (B) of 25 g/g or more while satisfying Equation 1 below:

$$\text{Swollen gel rupture index} = \text{Swollen gel rupture rate under pressure } (A)/\text{Water-retention ability } (B) \leq 1.5 \quad \text{[Equation 1]}$$

(wherein the swollen gel rupture rate under pressure (A) refers to a percentage of the swollen gel which is obtained by introducing a super-absorbent polymer into a teabag, sealing the teabag, immersing the teabag in 0.9% by weight saline, swelling the polymer for 30 minutes, dehydrating the treated product by a centrifuge under 250 G condition for 3 minutes, providing the remaining super-absorbent swollen gel in a net having 177 micron mesh holes, sealing the open side of the net, placing the net in a holder of the centrifuge, and rotating the net under 1500 G condition for 5 minutes to rupture the swollen gel and allow the same to escape out of the net mesh;

the water-retention ability (B) refers to an absorbency to weight of the initial absorbent polymer, which is obtained by immersing a super-absorbent polymer in 0.9% by weight saline, swelling the polymer for 30 minutes and partially removing water contained in the swollen gel by a centrifuge under 250 G condition for 3 minutes).

(4) The super-absorbent polymer according to the above (3), wherein it satisfies Equation 2 below:

$$\text{Swollen gel rupture index} \leq 1.0. \quad \text{[Equation 2]}$$

(5) The super-absorbent polymer according to the above (3), wherein it satisfies Equation 3 below:

$$\text{Swollen gel rupture index} \leq 0.5 \quad \text{[Equation 3]}$$

(6) The super-absorbent polymer according to the above (1), wherein the base resin is acrylic polymer.

(7) The super-absorbent polymer according to the above (3), wherein the water-retention ability is 33 g/g or more.

The super-absorbent polymer prepared according to the preparation method of the present invention may enable uniform internal cross-linkage so as to remarkably improve shape rupture under pressure while maintaining excellent absorption ability.

DETAILED DESCRIPTION

The present invention discloses a super-absorbent polymer which satisfies Equation 1 to remarkably improve shape rupture under pressure while maintaining excellent absorption ability, as well as a method of preparing the same.

Hereinafter, exemplary embodiments of the super-absorbent polymer of the present invention will be described in detail.

In the present disclosure, the super-absorbent polymer refers to a water-swelling and water-insoluble polymer gelling agent. Herein, the water-swelling property means that an absorbency under non-pressure (centrifuge retention capacity (CRC)) defined in ERT 442.2-02 is 5 g/g or more, and the water-insoluble property means that an amount of extractables (Ext) defined in ERT 470.2-02 ranges from 0 to 50% by weight ('wt. %').

The absorbency under pressure (AUL) means an absorbency (g/g) after swelling under pressure (load), and in the present disclosure, the absorbency under 0.3 psi pressure to saline refers to an absorbency after swelling the absorbent polymer in saline containing 0.9 wt. % sodium chloride under 0.3 psi pressure for 60 minutes, and may be determined according to Equation 4 below:

Absorbency under pressure (g/g)=(Weight of absorbent polymer after absorption (g)−Weight of absorbent polymer before absorption (g))/Weight of resin before absorption (g).   [Equation 4]

In the present disclosure, the absorbency under non-pressure (CRC) refers to an absorbency under non-pressure to 0.9 wt. % saline for 30 minutes, and may be determined according to Equation 5 below.

Absorbency under non-pressure (g/g)={(Absorbent gel+Weight of teabag (g))−Weight of empty teabag (g)}/Weight of dried resin (g)   [Equation 5]

In the present disclosure, "extractables" refer to acryl oligomer component (liquid eluent) dissolved in water, and may be determined according to Equation 6 below by immersing an absorbent polymer in water with 100 times the weight of the resin for 1 hour, filtering the prepared water-soluble solution through a filter under pressure, dehumidifying and drying the extracted component.

Extractables (wt. %)=(Weight of extracted component/Weight of initial dry-absorbent polymer)*100   [Equation 6]

<Super-Absorbent Polymer>

According to one embodiment of the present invention, the super-absorbent polymer has a water-retention ability (B) of 25 g/g or more while satisfying Equation 1 below.

Swollen gel rupture index(=Swollen gel rupture rate under pressure ($A$)/Water-retention ability ($B$))≤1.5   [Equation 1]

wherein the swollen gel rupture rate under pressure (A) refers to a percentage of the swollen gel which is obtained by introducing a super-absorbent polymer into a teabag, sealing the teabag, immersing the teabag in 0.9% by weight saline, swelling the polymer for 30 minutes, dehydrating the treated product by a centrifuge under 250 G condition for 3 minutes, providing the remaining super-absorbent swollen gel in a net having 177 micron mesh holes, sealing the open side of the net, placing the net in a holder of the centrifuge, and rotating the net under 1500 G condition for 5 minutes to rupture the swollen gel and allow the same to escape out of the net mesh; and the water-retention ability (B) refers to an absorbency to weight of the initial absorbent polymer, which is obtained by immersing a super-absorbent polymer in 0.9% by weight saline, swelling the polymer for 30 minutes and partially removing water contained in the swollen gel by a centrifuge under 250 G condition for 3 minutes.

As a result of finding that the swollen gel rupture rate under pressure (A) and the water-retention ability (B) are associated with uniformity in surface cross-linkage of the super-absorbent polymer, an embodiment of the present invention has been devised. When the super-absorbent polymer satisfies the above Equation 1, the polymer may be uniformly surface cross-linked and exhibit small shape rupture even when a pressure is applied. Therefore, when the super-absorbent polymer is used as a product such as a disposable diaper, or hygienic products, skin festering may be prevented during the use of product, a feeling of use may be improved, and excellent gel strength and improvement of absorption ability may be expected.

If the swollen gel rupture index exceeds 1.5, the gel strength may be considerably decreased to cause drastic reduction in absorption ability due to gel rupture. When the swollen gel rupture index is 1.5 or less, particularly, 1 or less, and more particularly, 0.5 or less, the gel strength may be noticeably improved to inhibit reduction in absorption ability.

Further, according to one embodiment of the present invention, the super-absorbent polymer may have the water-retention ability (B) of 25 g/g or more. If the water-retention ability is less than 25 g/g, ability for retention of absorbed moisture may be low and gel blocking may occur. In such an aspect, the water-retention ability (B) is, for example, 33 g/g or more.

For the super-absorbent polymer, whether or not Equation 1 is satisfied may be identified by a variety of methods. For example, Equation 1 may be satisfied according to different methods such as control of specific types and/or contents of monomers used in the super-absorbent polymer, use of a specific cross-linking agent in the polymerization of the super-absorbent polymer, control of content of the cross-linking agent, or addition of a cross-linking process, etc.

In one embodiment of the present invention, the super-absorbent polymer may be prepared by grinding a base resin, and then, surface cross-linking the same.

The base resin may include, for example, one or two or more selected from a group consisting of: acrylic polymer; hydrolysate of starch-acrylonitrile graft polymer; starch-acrylic acid graft polymer or a neutralization product thereof; a carboxymethyl cellulose cross-linked product; a saponification product of vinyl acetate-acrylic acid ester copolymer; acrylonitrile copolymer, or hydrolysate of acrylamide copolymer or a cross-linked product thereof; carboxyl group containing cross-linked polyvinyl alcohol modified product; a cross-linked product of cationic monomer; a cross-linked product of 2-acrylamide-2-methylpropane sulfonic acid and acrylic acid; cross-linked isobutylene-maleic anhydride copolymer; or the like. Among these, acrylic polymer may be used.

Hereinafter, acrylic polymer used as a base resin will be described in detail, but it is not limited thereto.

The acrylic polymer may be a homopolymer or copolymer of acrylic monomers.

In the present disclosure, the acrylic monomer refers to acrylic acid or a salt thereof. Acrylic acid salts may include, for example, alkali-metal salt, ammonium salt, alkylamine salt, etc., but it is not limited thereto.

According to one embodiment of the present invention, the acrylic copolymer may be polymerized while further including any unsaturated monomer known in the related art other than the above-described acrylic monomer.

For example, acid group containing monomers such as β-acryloyloxy propionic acid, methacrylic acid, maleic anhydride, fumaric acid, crotonic acid, itaconic acid, vinyl sulfonic acid, 2-(meth)acrylamide-2-methylpropane sulfonic acid, (meth)acryloxyalkane sulfonic acid, etc., and alkali-metal salts, aluminum salts, and alkylamine salts thereof; water-soluble or water-insoluble unsaturated monomers such as N-vinyl-2-pyrrolidone, N-vinyl acetamide, (meth)acrylamide, N-isopropyl(meth)acrylamide, N,N-dimethyl(meth)acrylamide, 2-hydroxyethyl(meth)acrylate, methoxypolyethylene glycol(meth)acrylate, polyethyleneglycol(meth)acrylate, isobutylene, lauryl(meth)acrylate, etc.; or the like, may be exemplified. These compounds may be used alone or in combination of two or more thereof.

In the case of the acrylic polymer according to one embodiment of the present invention, a content of acrylic monomer is not particularly limited but, for example, the acrylic monomer may be included and polymerized in an amount of 70 to 100 mol. %, and for example, 90 to 100 mol. % to the total monomer.

An acid group containing unsaturated monomer such as acrylic monomer may be used after neutralization to have a pH value around a neutral level in aspects of physical properties and pH. For example, the monomer may be neutralized using an alkaline compound such as sodium hydroxide, potassium hydroxide, lithium hydroxide, ammonium carbonate, sodium carbonate, potassium carbonate, ammonium phosphate, sodium phosphate, etc. A rate of neutralization of acid groups (mol. % of neutralized acid groups among total acid groups) generally ranges from 20 to 100 mol. %, particularly, 30 to 95 mol. %, and more particularly, 40 to 80 mol. %. If the rate of neutralization is less than 20 mol. %, absorption ability of the resin may be deteriorated. If the rate of neutralization exceeds 80 mol. %, most of the resin may be dissolved in water.

<Method of Preparing Super-Absorbent Polymer>

In addition, an embodiment of the present invention provides a method of preparing the above-described super-absorbent polymer according to the embodiment of the present invention. Hereinafter, the method of preparing a super-absorbent polymer according to one embodiment of the present invention will be described in detail. The following embodiment for the preparation method of the present invention as well as the above description are proposed to more concretely understand the technical spirit of the present invention, therefore, it is not construed that the present invention is particularly limited to the description of the following embodiment.

The method of preparing a super-absorbent polymer according to one embodiment of the present invention may include polymerization, drying, grinding and surface cross-linking processes.

The polymerization process may include the following steps:

polymerization by using a polyfunctional nitroxide mediated radical polymerization initiator having at least three substituents represented by Formula 1 below:

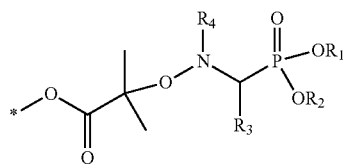

[Formula 1]

wherein * denotes a dangling bond, and $R_1$, $R_2$, $R_3$ and $R_4$ are each independently alkyl group having 1 to 6 carbon atoms;

substituting a terminal of the polymer prepared in the polymerization step with maleic anhydride; and cross-linking each maleic anhydride terminal of different polymers prepared in the substitution step by using alkylenediamine having 2 to 8 carbon atoms.

The polymerization step in the polymerization process according to one embodiment of the present invention may be conducted by polymerizing a polymer composition including: a polymeric compound containing an acrylic monomer; and a nitroxide mediated radical polymerization initiator which contains at least three substituents represented by above Formula 1.

The polymeric compound containing an acrylic monomer may include the above-described acrylic monomer and an unsaturated monomer known in the related art.

In the polymerization step, the nitroxide mediated radical polymerization initiator containing at least three substituents represented by Formula 1 is used for preparing the acrylic copolymer and has characteristics that the initiator is activated to allow polymerization during heating and, even if the temperature is decreased, is not quenched but capped at the terminal of polymer and activated again during re-heating ('living radical polymerization').

The nitroxide mediated radical polymerization initiator according to one embodiment of the present invention may be prepared using a compound, which can determine the number of functional groups of the nitroxide mediated radical polymerization initiator, as well as a nitroxide initiator. The number of such functional groups may be at least 3, and the upper limit of the functional groups is not particularly limited but, for example, may be 4, 5, 6, 7, 8, 9 or 10.

The compound capable of determining the number of functional groups in the nitroxide mediated radical polymerization initiator may include, for example, pentaerythritol tetrakis (2-bromoisobutyrate), (1,1,1-tris(2-bromoisobutyryloxymethyl)ethane), dipentaerythritol hexakis(2-bromoisobutyrate), or the like.

The nitroxide initiator may include, for example, N-tert-butyl-N-(1-diethyl-phosphono-2,2-dimethylpropyl)nitroxide, or the like.

The nitroxide mediated radical polymerization initiator prepared as described above may contain at least three substituents represented by Formula 1 below.

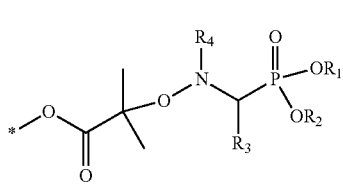

[Formula 1]

wherein * denotes a dangling bond, $R_1$, $R_2$, $R_3$ and $R_4$ are each independently alkyl group having 1 to 6 carbon atoms, and for example, $R_1$ and $R_2$ may be each ethyl group and $R_3$ and $R_4$ are each tert-butyl group.

An amount of the nitroxide mediated radical polymerization initiator is not particularly limited but, for example, may range from 0.001 to 2% by mole ('mol. %'), and, for example, 0.01 to 0.1 mol. % to a total monomer included in the polymer to be polymerized. If the amount of the polymerization initiator is less than 0.001 mol. %, unreacted monomer residue may be remained in a large quantity, and if it exceeds 2 mol. %, polymerization may be difficult to control.

The acrylic monomer used herein may be the same monomer as described above. Further, the unsaturated monomer described above may be used for copolymerization. The acrylic monomer may be used in a content within the above range.

After the polymerization step, a step of substituting the terminal of the obtained polymer with maleic anhydride may be conducted.

During the substitution step, a structure in a circle of Formula 1-1 present at the terminal of the polymer produced in the polymerization step is substituted with maleic anhydride, therefore, a reactive group reacting with a cross-linking agent in the following cross-linking step may be introduced at the terminal of the polymer.

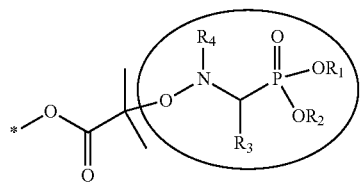

[Formula 1-1]

wherein * denotes a dangling bond, and $R_1$, $R_2$, $R_3$ and $R_4$ are each independently alkyl group having 1 to 6 carbon atoms.

More particularly, the nitroxide mediated radical polymerization initiator may be at least one compound represented by Formula 2-4 below, but it is not limited thereto.

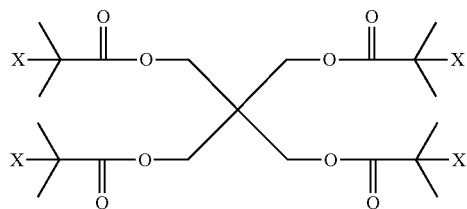

[Formula 2]

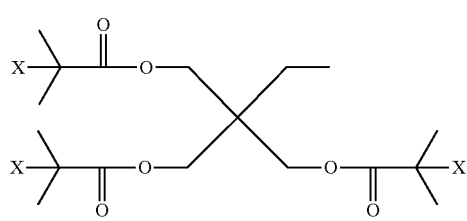

[Formula 3]

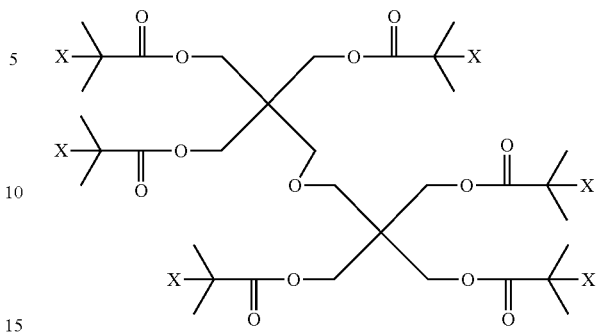

[Formula 4]

wherein x is a structure represented by Formula 5 below.

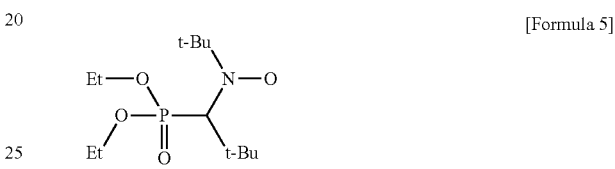

[Formula 5]

wherein Et is an ethyl group, and t-Bu is a tert-butyl group.

Next, a cross-linking step may be conducted using alkylenediamine having 2 to 8 carbon atoms, in order to cross-link each maleic anhydride terminal of different polymers prepared in the substitution step.

The alkylenediamine has amino groups at both ends of a molecule and thus may induce a coupling bond between the polymers obtained through the polymerization and substitution steps. Accordingly, a cross-linking network may be formed and make it possible to obtain a uniform cross-linkage structure of the absorbent polymer.

The alkylenediamine having 2 to 8 carbon atoms may include, for example, ethylenediamine, 1,3-propanediamine, 1,4-butanediamine, 1,5-pentanediamine, 1,6-hexanediamine, 1,7-heptanediamine, 1,8-octanediamine, or the like, but it is not limited thereto. These may be used alone or in combination of two or more thereof. For example, 1,5-pentanediamine is used.

As described above, when a base resin is prepared through polymerization, substitution and cross-linking steps, the base resin may be uniformly cross-linked to remarkably improve shape rupture under pressure while maintaining excellent gel strength and absorption ability.

During the polymerization step, each polymer composition may have more suitable physical properties for polymerization when oxygen dissolved in a monomer component is substituted with an inert gas under inert gas atmosphere. Such an inert gas may be selected from, for example, nitrogen or argon gas.

The polymerization of the polymer composition may be performed through thermal polymerization, in particular, may be conducted by a process of polymerizing at a temperature of 100 to 150° C. for 1 to 24 hours.

The base resin obtained in the polymerization process may be ground and, optionally, classified to provide a granular base resin.

A particle size of the granular base resin is not particularly limited but, for example, an average particle diameter may range from 150 to 800 μm, particularly, 150 to 600 μm, and more particularly, 180 to 500 μm. In addition, a ratio of particles having a particle diameter of less than 150 μm may range from 0 to 8 wt. %, and for example, 0 to 5 wt. % to a total weight of the granular base resin.

As necessary, the method of preparing a super-absorbent polymer according to one embodiment of the present invention may further include neutralization of the acrylic monomer.

The neutralization may be conducted by adding alkali in order to obtain a neutralization rate of acid groups (mol. % of neutralized acid groups among the total acid groups) in a range of, for example, 20 to 100 mol. %, particularly, 30 to 95 mol. %, and more particularly, 40 to 80 mol. %. If the rate of neutralization is less than 20 mol. %, absorption ability of the resin may be deteriorated, and if it exceeds 80 mol. %, the resin may be mostly dissolved in water.

The neutralization may be conducted before the cross-linking polymerization step, during the cross-linking polymerization step, after the cross-linking polymerization step, or through multiple steps.

As necessary, any typical process known in the related art may be further included to prepare a super-absorbent polymer.

For example, the present invention may further include: segmentation of the base resin obtained by the cross-linking polymerization; drying and grinding the segmented base resin to provide a granular base resin; and surface cross-inking the granular base resin.

For segmentation of the base resin, the present invention may use a grinder such as shear granulation machines, impact crushers, high speed rotation crushers, etc., but it is not limited thereto.

The grinder provided with at least one grinding device among cutting, shearing, impact and friction devices may be used. In particular, the grinder having the cutting or shearing device as a main function may be used. Further, a grinder provided with a compressor may be used in applications that are expected to involve strong shearing and cutting effects. Among other grinders listed above, a machine having multiple rotating blades and fixed blades to secure a shearing force can be used to achieve desired grinding effects.

Segmentation of the base resin may be performed to reach an average particle diameter of 1 to 20 mm.

A rotational velocity of the rotating blade may range from 3.0 to 200 m/sec, and more particularly, 5.0 to 150 m/sec.

The segmented base resin may undergo drying, for example, at a temperature of 50 to 250° C., and particularly, 100 to 170° C. If the drying temperature is less than 50° C., such lack of temperature may extend a time required for drying, hence reducing productivity.

The drying process may include any of drying methods to obtain desired water content, for example, heat drying, hot air drying, vacuum drying, infrared ray drying, microwave drying, dehydration using azeotrope with a hydrophobic organic solvent, high humidity drying using hot vapor, etc., but it is not limited thereto.

The segmented base resin may be ground by the same segmentation method as illustrated above.

The base resin may be ground to have an average particle diameter of, for example, 150 to 800 μm, particularly, 150 to 600 μm, and more particularly, 180 to 500 μm. A rate of particles having a particle diameter of less than 150 μm may range from 0 to 8 wt. %, and particularly, 0 to 5 wt. % to a total weight of the granular base resin.

Thereafter, the surface of the granular base resin may be subjected to cross-linking.

According to the present invention, surface cross-linking means that a cross-linking density near the surface of a particle is more increased than the inside of the particle. More particularly, the surface cross-linking refers to an operation to form a new cross-linkage bond by adding a compound (surface cross-linking agent) containing at least two functional groups, which can react with an acid group or a salt thereof (for example, a carboxyl group or a salt thereof) in the granular base resin, to the surface of the particle. By performing the surface cross-linking process, absorption ability under pressure may be improved.

The surface cross-linking step may be conducted, for example, at a temperature of 150 to 250° C. for 1 minute to 4 hours.

The surface cross-linking agent is not particularly limited but may include any surface cross-linking agent known in the related art, for example: (i) polyalcohol compounds such as 1,3-propanediol, 1-methyl-1,3-propanediol, 2-methyl-1,3-propanediol, ethylene glycol, diethyleneglycol, triethylene glycol, tetraethylene glycol, polyethyleneglycol, propylene glycol, dipropylene glycol, polypropylene glycol, 2,3,4-trimethyl-1,3-pentanediol, glycerin, polyglycerin, 2-butene-1,4-diol, 1,4-butanediol, 1,3-butanediol, 1,5-pentanediol, 1,6-hexanediol, meso-erythritol, D-sorbitol, 1,2-cyclohexane dimethanol, hexanediol, trimethylol propane, pentaerythritol, etc.;

(ii) epoxy compounds such as ethylene glycol diglycidyl ether, polyethylene glycol diglycidyl ether, glycerol polyglycidyl ether, propylene glycol diglycidyl ether, polypropylene glycol diglycidyl ether, etc.;

(iii) multivalent metal compounds such as hydroxides or chlorides of calcium, magnesium, aluminum, iron, etc.;

(iv) oxazolidinone compounds such as N-acyl oxazolidinone compound, 2-oxazolidinone compound, etc. (U.S. Pat. No. 6,559,239);

(v) alkylene carbonate compounds such as 1,3-dioxolan-2-on (also referred to as "ethylene carbonate"), 4-methyl-1,3-dioxolan-2-on, 4,5-dimethyl-1,3-dioxolan-2-on, 4,4-dimethyl-1,3-dioxolan-2-on, 4-ethyl-1,3-dioxolan-2-on, 4-hydroxymethyl-1,3-dioxolan-2-on, 1,3-dioxan-2-on, 4-methyl-1,3-dioxan-2-on, 4,6-dimethyl-1,3-dioxan-2-on, 1,3-dioxetan-2-on, etc. (U.S. Pat. No. 5,409,771);

(vi) oxetane compounds (3-ethyl-3-hydroxymethyl oxetane) and cyclic urea compounds (2-imidazolidinone) (U.S. Patent Publication No. 2002/0072471);

(vii) aminoalcohol compounds such as ethanolamine, diethanolamine, triethanolamine, etc. These compounds may be used alone or in combination of two or more thereof.

An amount of the surface cross-linking agent used herein is not particularly limited but, for example, may range from 0.001 to 10 wt. parts, and particularly, 0.01 to 5 wt. parts to 100 wt. parts of the granular base resin. When the surface cross-linking agent is used in the above content, the absorbency under pressure may be achieved.

Hereinafter, exemplary embodiments are proposed to more concretely describe the present invention. However, the following examples are only given for illustrating the present invention and those skilled in the art will obviously understand that various alterations and modifications are possible within the scope and spirit of the present invention. Such alterations and modifications are duly included in the appended claims.

PREPARATIVE EXAMPLE (1) Preparation of Nitroxide Mediated Radical Polymerization Initiator 1 g of pentaerythritol tetrakis (2-bromoisobutyrate), 1 g of N-tert-butyl-N-(1-diethyl-phosphono-2,2-dimethylpropyl) nitroxide, 0.01 g of copper(2) triflate ($Cu(OTf)_2$), 0.02 g of copper powders, 0.05 g of 4,4'-dinonyl-2,2'-dipyridyl (Nbpy), and 10 ml of benzene were added to a Schlenk flask, and deoxygenated using a nitrogen gas for 20 minutes. Then, after heating the product at 70° C. for 12 hours, column chromatography was performed using a mixed solution of hexane and ethyl acetate, thereby preparing 1.5 g of a nitroxide mediated radical polymerization initiator.

(2) Preparation of Nitroxide Mediated Radical Polymerization Initiator

The same procedures as described in Preparative Example 1 were conducted to prepare a nitroxide mediated radical polymerization initiator except that 1,1,1-tris(2-bromoisobutyryloxymethyl)ethane was used instead of pentaerythritol tetrakis (2-bromoisobutyrate) in Preparative Example 1.

(3) Preparation of Nitroxide Mediated Radical Polymerization Initiator

The same procedures as described in Preparative Example 1 were conducted to prepare a nitroxide mediated radical polymerization initiator except that dipentaerythritol hexakis(2-bromoisobutyrate) was used instead of pentaerythritol tetrakis (2-bromoisobutyrate) in Preparative Example 1.

EXAMPLE 1

After introducing 1 g of the nitroxide mediated radical polymerization initiator prepared in Preparative Example 1 into a Schlenk flask, a first polymerization process was conducted by adding 40 g of acrylic acid and 100 ml of 1,4-dioxane and heating the same at a temperature of 120° C. for 2 hours.

Then, a substitution process was further conducted by adding 1 equivalent maleic anhydride to the number of chains in polyacrylic acid to the polymer formed through the first polymerization process and heating the same at a temperature of 120° C. for 2 hours.

The polymer formed through the substitution process was precipitated in ethyl ether, followed by drying the same at room temperature.

20 g of the dried polymer powders were dissolved in 50 ml of 1,4-dioxane, 1,5-pentanediamine as a cross-linking agent was added to the solution, followed by heating the same at a temperature of 100° C. for 3 hours, thereby preparing a cross-linked acrylic copolymer.

After then, 50 ml of sodium hydroxide (corresponding to 0.7 mole) to the total monomer included and polymerized in the polymer was dissolved in water to prepare a sodium hydroxide solution, and this solution was added to the acrylic copolymer obtained through a cross-linking process in order to perform neutralization.

The prepared base resin was finely segmented using a shear force for 30 minutes, the segmented base resin was spread with a thickness of about 30 mm on a stainless wire gauze having a hole size of 600 μm and dried in a hot air oven at 160° C. for 5 hours. Then, the dried product was ground using a grinder, classified by a standard ASTM net mesh to prepare a granular base resin having a particle diameter of 150 μm to 800 μm.

A 10 wt. % solution of ethylene glycol diglycidyl ether in water was added to the prepared granular base resin in an amount of 2 wt. % to a total weight of the base resin, followed by a reaction while drying the same in a hot air oven at 160° C. under a relative humidity of 1.5% for 60 minutes. The dried power was classified by a standard ASTM net mesh, thereby preparing a super-absorbent polymer having a particle diameter of 150 μm to 800 μm.

EXAMPLE 2

As shown in Table 1, the same procedures as described in Example 1 were conducted to prepare a super-absorbent polymer except that the nitroxide mediated radical polymerization initiator prepared in Preparative Example 2 was used instead of the nitroxide mediated radical polymerization initiator.

EXAMPLE 3

As shown in Table 1, the same procedures as described in Example 1 were conducted to prepare a super-absorbent polymer except that the nitroxide mediated radical polymerization initiator prepared in Preparative Example 3 was used instead of the nitroxide mediated radical polymerization initiator.

COMPARATIVE EXAMPLE 1

The super-absorbent polymer obtained from Haggis premier product manufactured by Yuhan Kimberly Co.

COMPARATIVE EXAMPLE 2

The super-absorbent polymer obtained from Pampers Baby Dry product manufactured by P & G Co.

COMPARATIVE EXAMPLE 3

40 g of acrylic acid, 16 g of sodium hydroxide, 1 g of t-butyl hydroperoxide as a polymerization initiator, trimethylolpropane trimethacrylate (TMPTMA) as an internal cross-linking agent were added to a Schlenk flask, and deoxygenated for 20 minutes while introducing a nitrogen gas. After reducing heat of neutralization generated during neutralization through a cooling device, a polymerization process for heating the product at a temperature of 120° C. was conducted, thereby preparing a super-absorbent polymer.

COMPARATIVE EXAMPLE 4

As shown in Table 1, the same procedures as described in Comparative Example 3 were conducted to prepare a super-absorbent polymer except that sodium persulfate was used instead of the polymerization initiator.

TABLE 1

| Section | Polymerization initiator (A) Component | Polymerization initiator (A) Content (g) | Polymerization step [reaction condition] [temperature, time] | Substitution step [reaction condition] [temperature, time] | Cross-linking step [reaction condition] [temperature, time] |
|---|---|---|---|---|---|
| Example 1 | A-1 | 1 | [120° C., 2 hours] | [120° C., 1 hour] | [100° C., 3 hours] |

TABLE 1-continued

| Section | Polymerization initiator (A) Component | Con- tent (g) | Polymer- ization step [reaction condition] [temperature, time] | Substi- tution step [reaction condition] [temperature, time] | Cross- linking step [reaction condition] [temperature, time] |
|---|---|---|---|---|---|
| Example 2 | A-2 | 1 | [120° C., 2 hours] | [120° C., 1 hour] | [100° C., 3 hours] |
| Example 3 | A-3 | 1 | [120° C., 2 hours] | [120° C., 1 hour] | [100° C., 3 hours] |
| Comparative Example 1 | Haggis premier (Yuhan Kimberly Co.) | | | | |
| Comparative Example 2 | Pampers baby dry (P&G Co.) | | | | |
| Comparative Example 3 | A-4 | 1 | [120° C., 2 hours] | — | — |
| Comparative Example 4 | A-5 | 1 | [120° C., 2 hours] | — | — |

A-1: nitroxide mediated radical polymerization initiator in Preparative Example 1
A-2: nitroxide mediated radical polymerization initiator in Preparative Example 2
A-3: nitroxide mediated radical polymerization initiator in Preparative Example 3
A-4: t-butyl hydroperoxide
A-5: sodium peroxide

EXPERIMENTAL EXAMPLE (1) Calculation of Swollen Gel Rupture Index

After placing 0.2 g of the absorbent polymer prepared in each of the examples and comparative examples in a teabag with a size of 10 cm width×10 cm length and sealing the same, the teabag was immersed in 200 ml of 0.9 wt. % saline to swell the same for 30 minutes.

After 30 minutes, the teabag was dehydrated in a centrifuge under 250 G condition for 3 minutes. Then, 1 g of the remaining super-absorbent swollen gel was put in a net having 177 microns mesh holes (2 cm width×3 cm length) and the open side of the net was sealed. The net was placed in a holder of the centrifuge and rotated under 1500 G condition for 5 minutes to rupture the swollen gel. After measuring a percentage of the swollen gel escaping out of the mesh, the measured value was defined as a swollen gel rupture rate under pressure (A).

Next, after swelling 0.2 g of the absorbent polymer prepared in each of the examples and comparative examples in 200 ml of 0.9 wt. % saline for 30 minutes, water contained in the swollen gel was partially removed by a centrifuge under 250 G condition for 3 minutes. Then, the absorbency to weight of the initial absorbent polymer was calculated and defined as a water-retention ability (B).

According to the definition of a swollen gel rupture index described above, a swollen gel rupture rate under pressure (A) was divided by the water-retention ability (B) to calculate the swollen gel rupture index.

(2) Measurement of Free Absorption Ability 1.0 g of the absorbent polymer prepared in each of the examples and comparative examples was put in a 250 mL beaker and 150 g of 0.9 wt. % saline was added thereto to absorb the polymer over 30 minutes. After 30 minutes, the formed gel was poured through a standard mesh net (#mesh 100 with a diameter of 90 mm), then left for 30 minutes, followed by removing unabsorbed saline. The weight of absorbed saline was measured and the measured value was defined as an absorption ability.

(3) Measurement of Absorbency Under Pressure (AUL) (EDANA WSP 242.2.R3)

After laying a polyester gauze on a sintered glass filter plate, 0.9 g of the absorbent polymer prepared in each of the examples and comparative examples was homogeneously spread thereon.

Thereafter, weights were put in the cylinder to apply 0.3 psi load to the absorbent polymer, and 0.9 wt. % saline was poured up to a height of the filter plate.

After 60 minutes, the weight of the absorbent polymer was weighed and the absorbency under pressure was calculated by Equation 4 below.

Absorbency under pressure (g/g)=(Weight of resin after absorption (g)−Weight of resin before absorption (g))/Weight of resin before absorption (g)  [Equation 4]

(4) Measurement of Absorbency Under Non-Pressure (CRC) (EDANA WSP 241.2.R3)

After introducing the absorbent polymer prepared in each of the examples and comparative examples into a teabag and sealing the same, the teabag was immersed in 0.9 wt. % saline for absorption for 30 minutes.

Next, after centrifuging the teabag in a centrifuge set up to 250 G for 3 minutes, the weight of teabag was measured.

For an empty teabag, the same procedures as described above were conducted to measure a weight of the empty teabag. With the measure value, the absorbency under non-pressure was calculated by Equation 5 below.

Absorbency under non-pressure (g/g)={(Weight of the absorbent gel+Teabag (g))−Weight of the empty teabag (g)}/Weight of dried resin (g)  [Equation 5]

(5) Measurement of Extractables

Extractables in the absorbent polymer were measured according to extraction under pressure.

2 g of the absorbent polymer prepared in each of the examples and comparative examples, which was dehumidified and dried at 80° C. for 3 hours, and 200 g of water were introduced into a planetary mixer (Unitec Co. Ltd.), and dissolved at 50 rpm for 1 hour.

The prepared water-soluble solution was fed to a container equipped with a 1.2 μm glass filter paper and slowly concentrated, while passing the solution through the filter at 35° C. under 5 psi using a nitrogen gas, then, the extracted component was dehydrated and dried. According to Equation 6 below, an amount of extractables was determined.

Extractables (wt. %)=(Weight of extracted component/Weight of initial dry and absorbent polymer)*100  [Equation 6]

TABLE 2

| Section | Swollen gel rupture rate under pressure (A) (%) | Swollen gel rupture index | Free absorp- tion ability (g/g) | AUL (g/g) | CRC (g/g) | Ex- tract- able (wt. %) |
|---|---|---|---|---|---|---|
| Example 1 | 25 | 0.71 | 45 | 38 | 35 | 5 |
| Example 2 | 40 | 1.08 | 47 | 35 | 37 | 7 |
| Example 3 | 15 | 0.45 | 43 | 39 | 33 | 3 |
| Comparative | 56 | 2.07 | 38 | 28 | 27 | 18 |

TABLE 2-continued

| Section | Swollen gel rupture rate under pressure (A) (%) | Swollen gel rupture index | Free absorption ability (g/g) | AUL (g/g) | CRC (g/g) | Extractable (wt. %) |
|---|---|---|---|---|---|---|
| Example 1 | | | | | | |
| Comparative Example 2 | 53 | 1.89 | 32 | 24 | 28 | 19 |
| Comparative Example 3 | 65 | 2.50 | 39 | 27 | 26 | 23 |
| Comparative Example 4 | 55 | 1.90 | 31 | 25 | 29 | 17 |

Referring to Table 2, it can be seen that the super-absorbent polymer in each of the examples according to the present invention, which has a swollen gel rupture index within the inventive range, has lower extractables content, than the comparative examples, therefore, shape rupture under pressure is also considered to be less than the same in the comparative examples.

Further, since excellent free absorption ability, absorbency under pressure and absorbency under non-pressure were observed, it can be found that absorption ability has been improved.

While the present invention has been described with respect to the specific embodiments, it will be apparent to those skilled in the art that various changes and modifications may be made without departing from the spirit and scope of the invention as defined in the following claims.

What is claimed is:

1. A super-absorbent polymer having a water-retention ability (B) of 25 g/g or more while satisfying Equation 1 below:

Swollen gel rupture index=(Swollen gel rupture rate under pressure (A)/Water-retention ability (B))≤1.5    [Equation 1]

wherein the swollen gel rupture rate under pressure (A) refers to a percentage of the swollen gel which is obtained by introducing a super-absorbent polymer into a teabag, sealing the teabag, immersing the teabag in 0.9% by weight saline, swelling the polymer for 30 minutes, dehydrating the treated product by a centrifuge under 250 G condition for 3 minutes, providing the remaining super-absorbent swollen gel in a net having 177 micron mesh holes, sealing the open side of the net, placing the net in a holder of the centrifuge, and rotating the net under 1500 G condition for 5 minutes to rupture the swollen gel and allow the same to escape out of the net mesh;

the water-retention ability (B) refers to an absorbency to weight of the initial absorbent polymer, which is obtained by immersing a super-absorbent polymer in 0.9% by weight saline, swelling the polymer for 30 minutes and partially removing water contained in the swollen gel by a centrifuge under 250 G condition for 3 minutes.

2. The super-absorbent polymer according to claim 1, which satisfies Equation 2 below:

Swollen gel rupture index≤1.0.    [Equation 2]

3. The super-absorbent polymer according to claim 1, which satisfies Equation 3 below:

Swollen gel rupture index≤0.5.    [Equation 3]

4. The super-absorbent polymer according to claim 1, wherein the water-retention ability is 33 g/g or more.

* * * * *